(12) United States Patent
Kahn et al.

(10) Patent No.: US 11,471,097 B1
(45) Date of Patent: Oct. 18, 2022

(54) HARDWARE SENSOR SYSTEM FOR IMPROVED SLEEP DETECTION

(71) Applicants: Philippe Richard Kahn, Santa Cruz, CA (US); Arthur Kinsolving, Santa Cruz, CA (US); Mark Andrew Christensen, Santa Cruz, CA (US); Mihai Ionescu, Ben Lomond, CA (US); Sean Brooks Harre, Santa Cruz, CA (US); David Vogel, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Mihai Ionescu, Ben Lomond, CA (US); Sean Brooks Harre, Santa Cruz, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 97 days.

(21) Appl. No.: 16/601,561

(22) Filed: Oct. 14, 2019

Related U.S. Application Data

(60) Provisional application No. 62/745,976, filed on Oct. 15, 2018, provisional application No. 62/745,984, (Continued)

(51) Int. Cl.
*A61B 5/0205* (2006.01)
*A61B 5/00* (2006.01)
*A61G 7/05* (2006.01)

(52) U.S. Cl.
CPC .......... *A61B 5/4815* (2013.01); *A61B 5/4809* (2013.01); *A61B 5/4812* (2013.01); *A61B 5/0205* (2013.01); *A61G 7/05* (2013.01)

(58) Field of Classification Search
CPC ...... A61G 7/05; A61B 5/4809; A61B 5/4812; A61B 5/4815
See application file for complete search history.

(56) References Cited

U.S. PATENT DOCUMENTS 3,683,933 A * 8/1972 Mansfield .......... A61N 1/37518
    607/36
6,014,682 A * 1/2000 Stephen ............. H03H 17/0275
    708/313

(Continued)

OTHER PUBLICATIONS

Campbell, Appleinsider, "Apple buys sleep tracking firm Beddit" May 9, 2017. Retrieved from https://appleinsider.com/articles/17/05/09/apple-buys-sleep-tracking-firm-beddit (Year: 2017).

(Continued)

*Primary Examiner* — Nathan J Jenness
*Assistant Examiner* — Skylar Lindsey Christianson
(74) *Attorney, Agent, or Firm* — Nicholson De Vos Webster & Elliott LLP; Judith Szepesi

(57) ABSTRACT

A hardware sensor system comprising a piezo sensor outputting charge data corresponding to a motion, an insulated cable from the piezo sensor to a receiver, to transmit the charge data, an insulated charge to voltage converter on the receiver, the insulated charge to voltage converter converting the charge data to voltage data, an analog-to-digital converter to convert the voltage data to digital data, and an uploader to upload the data to a server for processing.

20 Claims, 7 Drawing Sheets

Related U.S. Application Data filed on Oct. 15, 2018, provisional application No. 62/745,978, filed on Oct. 15, 2018.

(56) References Cited

U.S. PATENT DOCUMENTS

| | | | |
|---|---|---|---|
| 7,139,342 B1* | 11/2006 | Phanse | H04B 3/23 |
| | | | 375/350 |
| 8,909,357 B2 | 12/2014 | Rawls-Meehan | |
| 2004/0071382 A1* | 4/2004 | Rich | G08B 13/124 |
| | | | 385/12 |
| 2007/0093722 A1 | 4/2007 | Noda et al. | |
| 2008/0269625 A1* | 10/2008 | Halperin | A61B 5/08 |
| | | | 600/508 |
| 2010/0010565 A1* | 1/2010 | Lichtenstein | A61N 1/32 |
| | | | 607/46 |
| 2011/0304240 A1* | 12/2011 | Meitav | H02N 2/181 |
| | | | 310/319 |
| 2013/0197857 A1* | 8/2013 | Lu | A61B 5/1122 |
| | | | 702/141 |
| 2014/0350351 A1 | 11/2014 | Halperin et al. | |
| 2015/0094544 A1* | 4/2015 | Spolin | A61B 5/6831 |
| | | | 600/301 |
| 2015/0164409 A1 | 6/2015 | Benson et al. | |
| 2015/0333950 A1* | 11/2015 | Johansson | H04L 27/3863 |
| | | | 375/349 |
| 2016/0287869 A1* | 10/2016 | Errico | H04M 1/21 |
| 2017/0188938 A1 | 7/2017 | Toh et al. | |
| 2018/0103770 A1 | 4/2018 | Nava et al. | |
| 2019/0044380 A1* | 2/2019 | Lausch | A61F 2/32 |
| 2019/0132570 A1* | 5/2019 | Chen | H04N 5/232 |

OTHER PUBLICATIONS

Crist, CNET "Samsung introduces SleepSense" Sept. 3, 2015. Retrieved from https://www.cnet.com/reviews/samsung-sleepsense-preview (Year: 2015).

Internet Archive, Withings "Sleep Tracking Mat" Nov. 22, 2018. Retrieved from https://web.archive.org/web/20181122024547/https://www.withings.com/us/en/sleep (Year: 2018).

* cited by examiner

HARDWARE SENSOR SYSTEM FOR IMPROVED SLEEP DETECTION

RELATED APPLICATION

The present application claims priority to U.S. Provisional Patent Application 62/745,976 filed on Oct. 15, 2018. The present application also claims priority to U.S. Provisional Patent Application No. 62/745,978 (8689P232Z) and U.S. Provisional Application No. 62/745,984 (8689P233Z) both filed on Oct. 15, 2019 and incorporates all three of those applications by reference in their entirety.

FIELD

The present invention relates to sleep sensors, and more particularly to an improved sleep detection system including sensor hardware.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

Therefore, it is useful for everyone to know more about how well they sleep.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A sleep monitoring system is described. The system includes analog and digital elements, which collect data from a sleeper and provide it for processing and analysis to a server system. In one embodiment, the sleep monitoring system includes a sensor which is designed to be placed under a user's mattress or mattress topper, or in a user's bedframe. In one embodiment, this sensor collects movement data, and sends it through an insulated cable to a receiver. In another embodiment, the data may be sent wirelessly. The receiver, which in one embodiment is positioned in proximity to the bed, receives the insulated cable or wireless signal, and converts the data to a digital signal. In one embodiment, the digital signal is uploaded to the server for further processing and analysis. The server analyzes the sleep data, and can be used to set the receiver's operation, as well as control the user's sleep environment, in one embodiment.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized, and that logical, mechanical, electrical, functional and other changes may be made without departing from the scope of the present invention. The following detailed description is, therefore, not to be taken in a limiting sense, and the scope of the present invention is defined only by the appended claims.

Figure 1:
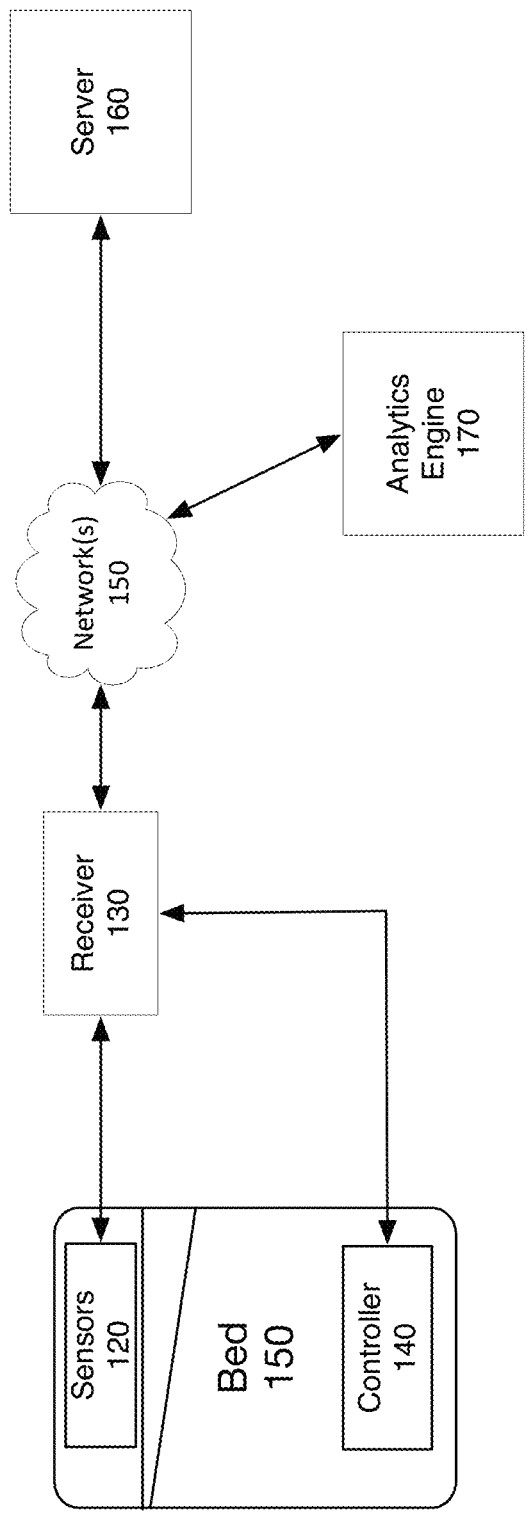
FIG. 1 is block diagram of one embodiment of a system in which the sensor system may be implemented.

FIG. 1 is block diagram of one embodiment of a system in which the sensor system may be implemented. The system includes a sleep analytics system 100 including sensors 120, receiver 130, server 160, and analytics engine 170. In one embodiment, the client portion of the sleep analytics system 100 is located in a user's home includes the sensors 120 and receiver 130.

In one embodiment, the receiver 130 is coupled to sensors 120 via a cable. In another embodiment the connection may be wireless, such as low power Bluetooth (BLE), Wi-Fi, or another type of wireless connection. In one embodiment, receiver 130 also may be coupled to a controller 140, which controls bed 150. In one embodiment, this connection is a wired connection. Alternatively, it may be a wireless connection.

In one embodiment, the sensors 120 may include one or more sensors positioned in bed 150 which are used to measure the user's sleep. In one embodiment, sensors 120 may include sensors which are not in bed 150 but positioned in the room in which the bed 150 is located. In one embodiment, one or more these additional sensors may be built into receiver 130. In one embodiment, there may be external sensors which may be coupled to receiver 130 either via wires or wirelessly. The receiver 130 collects data from the one or more sensors, for transmission to the server 160.

In one embodiment, the receiver 130 is coupled to the server 160 via a network 150. The server portion includes server 160 and analytics engine 170, which in one embodiment are located off-site, removed from the user. In another embodiment, the server may be a local system, such as a computer system running an application. The network 150 may be the Internet, and the receiver 130 may send data to the server via a wireless network, such as Wi-Fi or the cellular network. In one embodiment, server 160 and analytics engine 170 may be on the same physical device. In one embodiment, server and/or analytics engine 170 may include a plurality of devices. In one embodiment, one or both of the server 170 and the analytics engine 170 may be using cloud computing and may be implemented as a distributed system.

Figure 2:
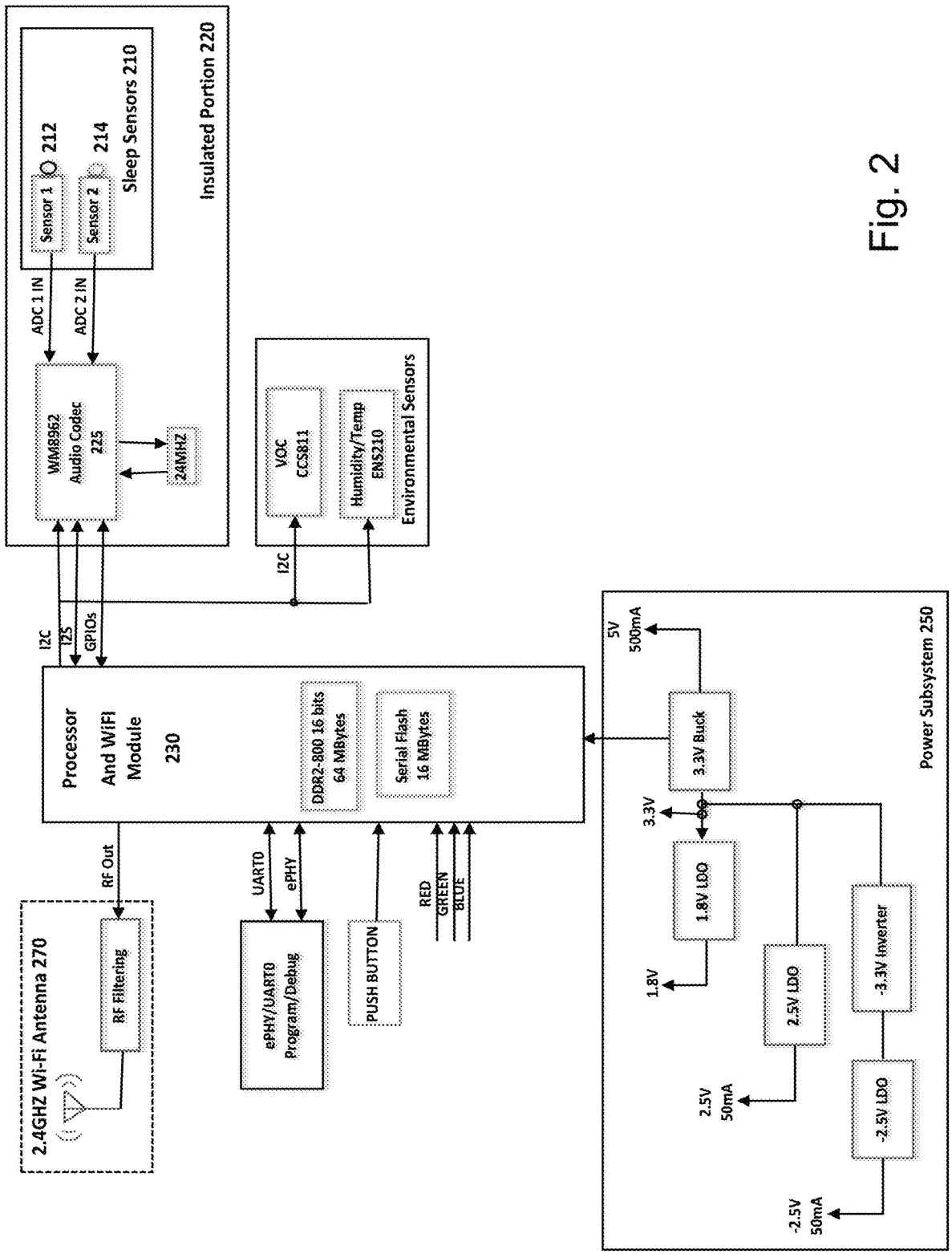
FIG. 2 is a block diagram of one embodiment of the sensor and receiver portion of the sensor system.

FIG. 2 is a block diagram of one embodiment of the sensor and receiver portion of the sensor system. In one embodiment, sleep sensors 210 include two sensors 212, 214, which are designed to be placed underneath a mattress, mattress topper, or mattress cover. In one embodiment, the sensors are piezoelectric sensors positioned on a hard foam surface to provide compressibility and support. In one embodiment, the sensors are coupled to an audio codec 225 to encode the data, for transmission to the server. By using audio codec, the data can be encoded in a way that provides 100% accuracy and a reduction in data size. In one embodiment, the receiver further includes additional environmental sensors 225. In one embodiment, the environmental sensors 225 may include a humidity and temperature sensor and a volatile organic compounds (VOC) sensor. Other sensors may also be included in the receiver.

In one embodiment, he encoded data from the sleep sensors 210 and the data from the environmental sensors 225 (which may also be encoded in some embodiments) are passed to a processor and Wi-Fi module 230. The processor and Wi-Fi module 230 sends the data to the server via a Wi-Fi connection 270. In another embodiment, the processor and Wi-Fi module 230 may be replaced by a separate processor and network access element. The Wi-Fi module may be replaced by a mobile network chip. In one embodiment, the processor and Wi-Fi module 230 includes a random access memory, such as DDR2, to buffer the data from the sensors, prior to transmission. In one embodiment, a flash memory may store the code for the processor 230.

In one embodiment, power subsystem 250 provides power to the processor 230, codec 225, and environmental sensors. In one embodiment, the power subsystem 250 provides a 3.3V power to the processor 230. In one embodiment, the power subsystem 250 also provides 1.8V to the audio codec 225, or other elements of the system. In one embodiment, the sleep sensors 210 provide their data as charge data between 2.5V and −2.5V. Thus, in one embodiment, the power subsystem handles voltages between −2.5V and 5V.

Figure 3:
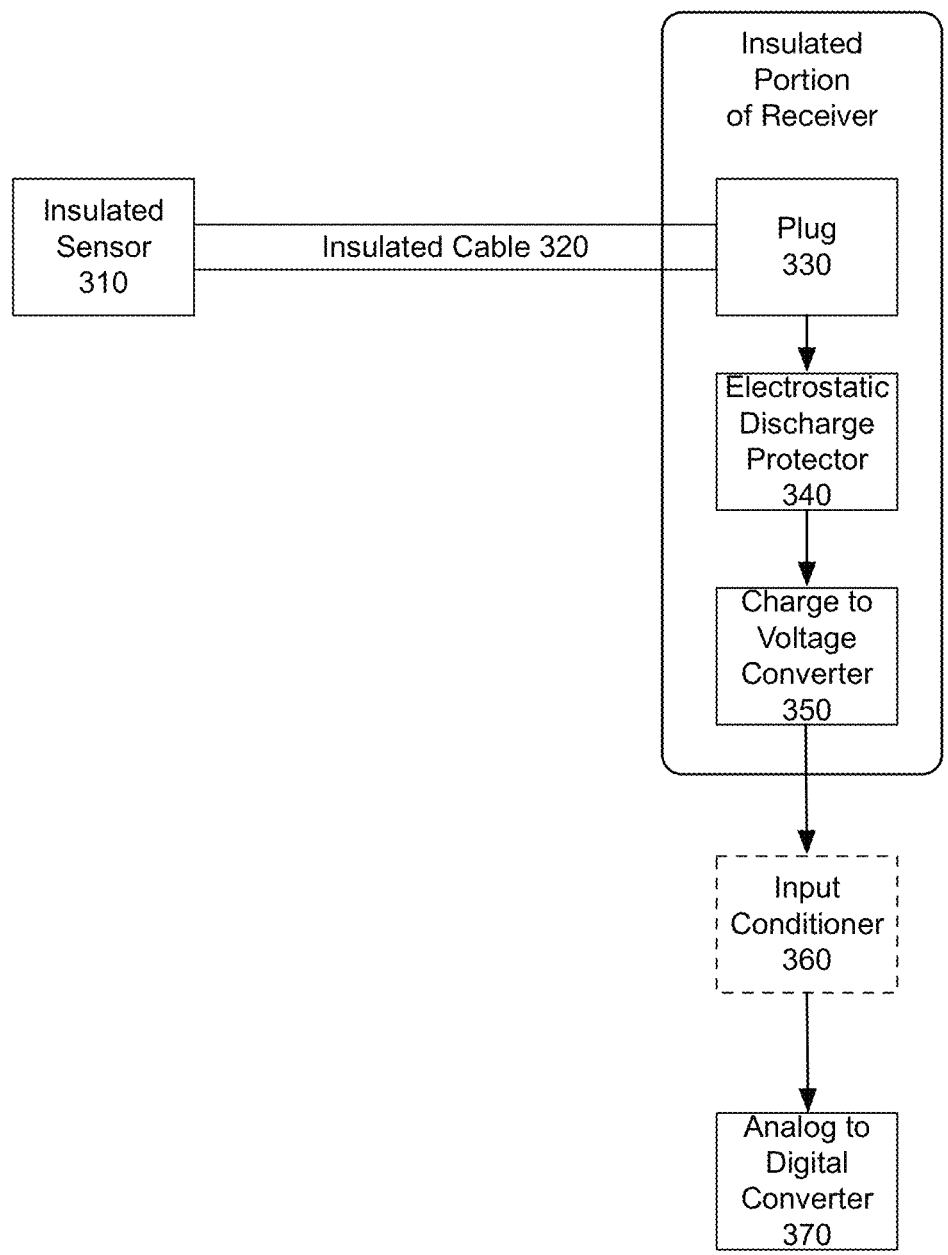
FIG. 3 is a block diagram of one embodiment of the first portion of the receiver and the A-to-D converter.

FIG. 3 is a block diagram of one embodiment of the first portion of the receiver and the A-to-D converter. In one embodiment, the system includes an insulated sensor 310. The insulated sensor is a piezo sensor, which is sensitive to movement. The sensor 310 itself is insulated, to ensure that it is not impacted by stray signals. Because the sensor 310 provides data as a voltage level, any noise impacting the sensor 310 may overwhelm the real data. In one embodiment, a ground connection is provided to the sensor 310 to provide insulation. The sensor 310 is coupled to the receiver 300 via cable 320, in one embodiment. In one embodiment, the cable 320 is a grounded cable. In one embodiment, the cable 320 is a custom shielded cable with two conductors.

The cable 320 connects to a plug 330 in receiver. In one embodiment, the plug is an insulated plug, to shield the data from the sensor from noise. In one embodiment, an electrostatic discharge protector (EDS) 340 is coupled to the line as well. A charge to voltage converter 350 converts the output of the sensors 310, which is charge data, into a voltage. The plug 330, EDS protector 340, and charge to voltage converter 350 all are on an insulated portion 220 of the receiver. In one embodiment, a custom metal enclosure provides the insulation. In one embodiment, the custom metal enclosure is grounded. In one embodiment, the receiver utilizes a three-prong plug, to request a grounded outlet. In one embodiment, the receiver verifies that the wall connection provides a proper ground. In one embodiment, the user may be alerted if the receiver is plugged into an ungrounded outlet. However, in one embodiment, the metal enclosure provides protection/insulation even when not properly grounded.

The output of the charge to voltage converter 350 is passed to an input conditioner, in one embodiment. The input conditioner 360 adjusts the voltage range of the signal. The voltage is then passed to an analog to digital converter 370, in one embodiment. This converts the analog sensor data into a digital signal. The output of the analog to digital converter 370 is encoded and sent to the server for analysis. In one embodiment, the digital signal is encoded to ensure error correction. The signal may also be compressed.

For simplicity this figure, and others, illustrate a single sensor and connection. In one embodiment, the system may include two sensors when configured to detect two sleepers. In one embodiment, the system may include more than two sensors. When additional sensors are used, they may be separately handled. In one embodiment, each sensor has a separate and substantially identical path. In another embodiment, multiple sensors may send their data to the receive through a shared path.

Figure 4:
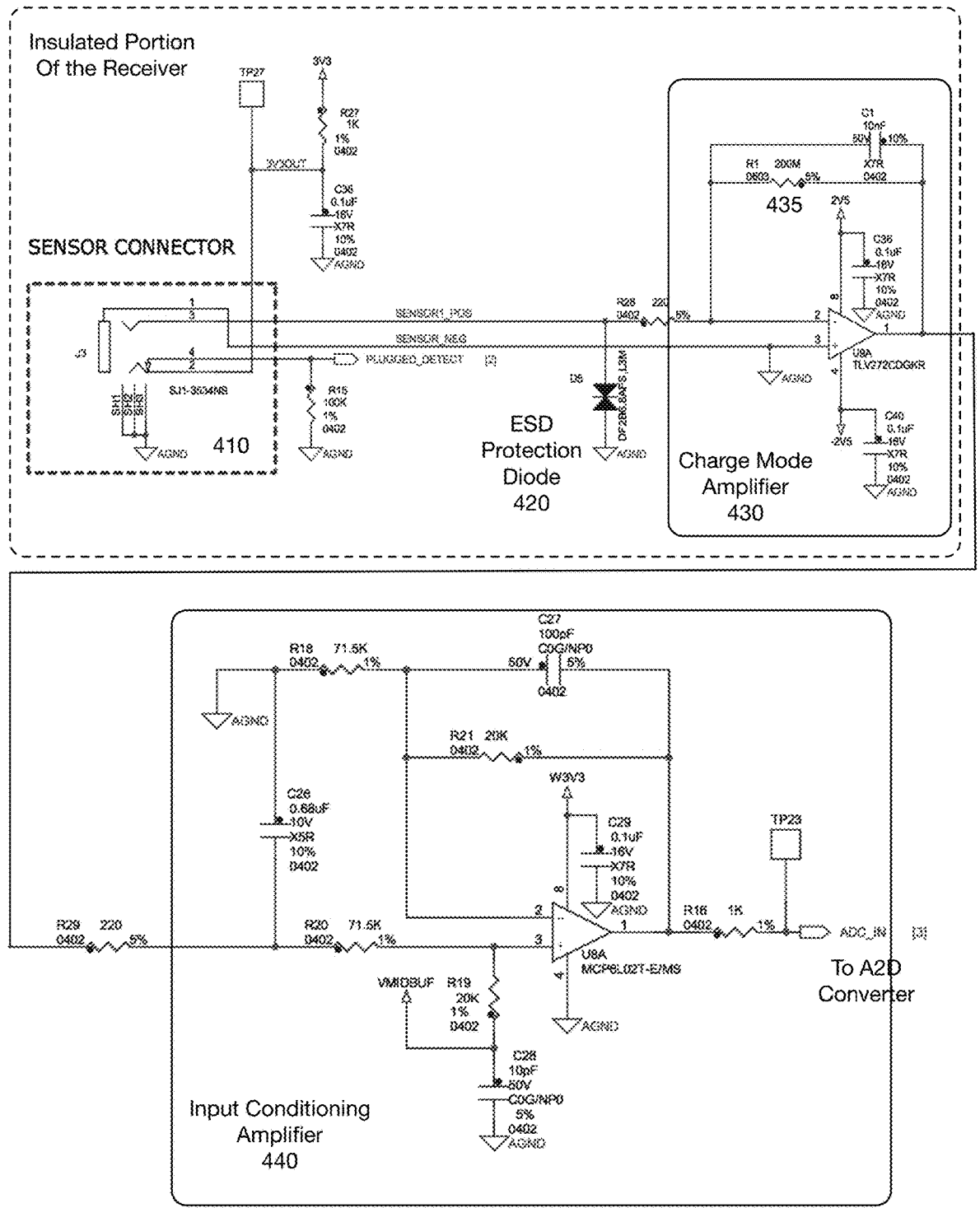
FIG. 4 is a circuit diagram of one embodiment of the first portion of the receiver.

FIG. 4 is a circuit diagram of one embodiment of the first portion of the receiver. The receiver includes the sensor connector 410 to which the cable is coupled. ESD protection diode 420 is tied to ground and protects against electrostatic discharge.

The charge mode amplifier 430 provides a charge to voltage conversion for the signal from the sensors. The charge mode amplifier is an op-amp with a negative feedback capacitor and a large resistor 435, converting the charge signal to a voltage output.

The voltage output from the charge mode amplifier 430 is passed to an input conditioning amplifier 440. The input conditioning amplifier is 440 an op-amp that adjusts the voltage range of the signal, for the analog-to-digital converter. In one embodiment, the input to the input conditioning amplifier a voltage value between −2.5V and 2.5V and adjusts it to 0V to 1.8V. In one embodiment, this element may be skipped if the Analog-to-Digital converter can handle the voltage range output by the charge mode amplifier 430.

Figure 5:
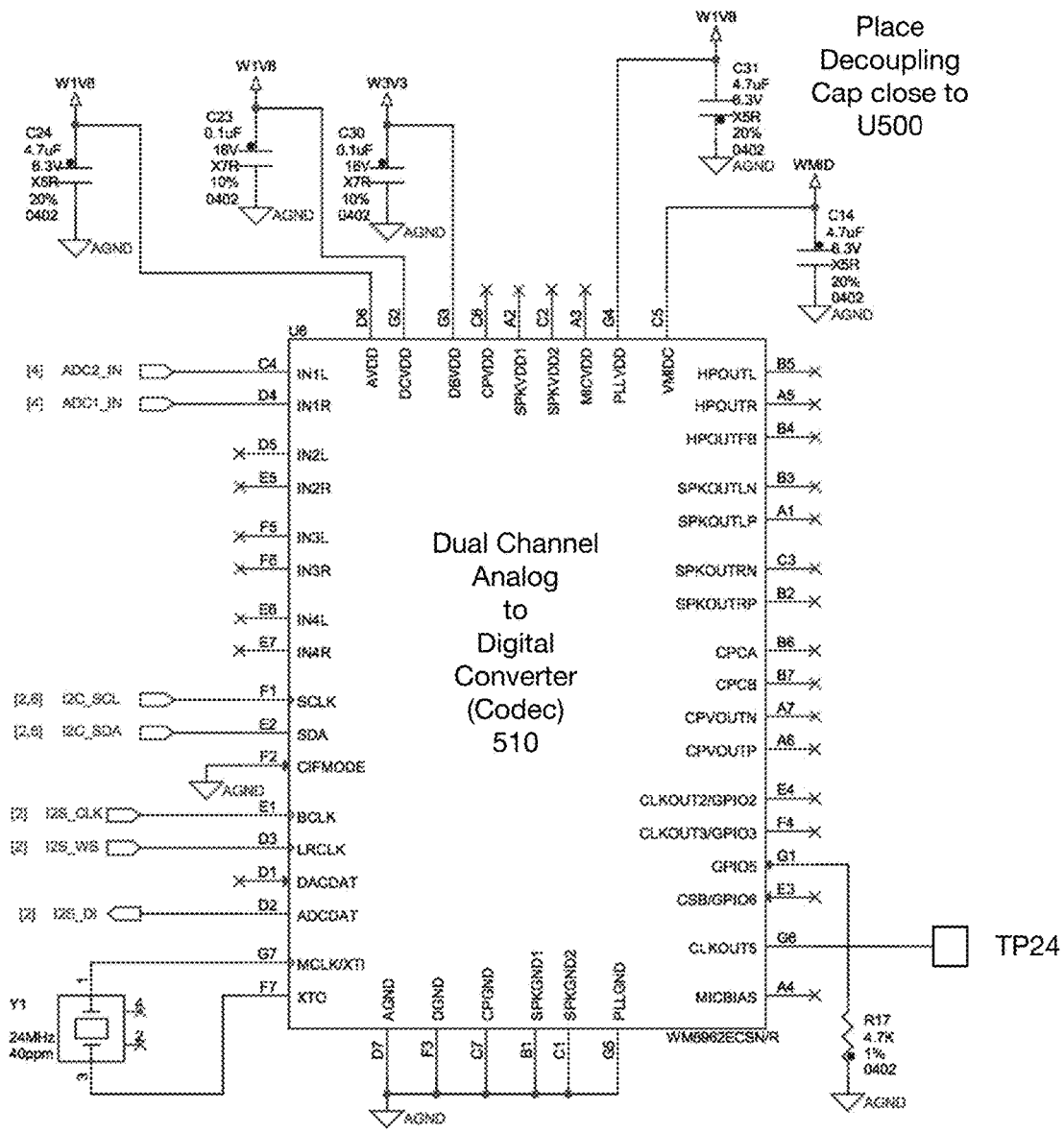
FIG. 5 is a circuit diagram of one embodiment of the A-to-D converter.
Figure 5:
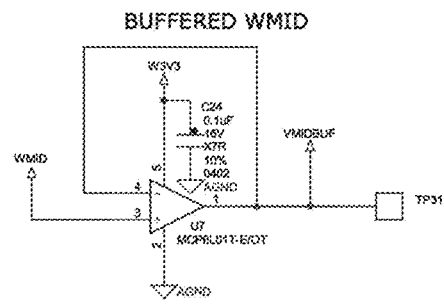

FIG. 5 is a circuit diagram of one embodiment of the A-to-D converter. In one embodiment, for simplicity and to ensure that the two signals are processed in a synchronized manner, the A-to-D converter 510 is an Audio CODEC, which provides concurrent sampling of two channels, at 24 bits. This maintains time alignment between data from the two sensors. Of course, another type of analog-to-digital converter may be used. In one embodiment, the A-to-D converter used should provide at least two channels, and at least an 18-bit rate sampling. This is the last portion of the receive which is analog. The output of the A-to-D converter is digital and is passed to the digital portion of the receiver. In one embodiment, the analog portion of the receiver and the digital portion are on separate substrates.

Figure 6:
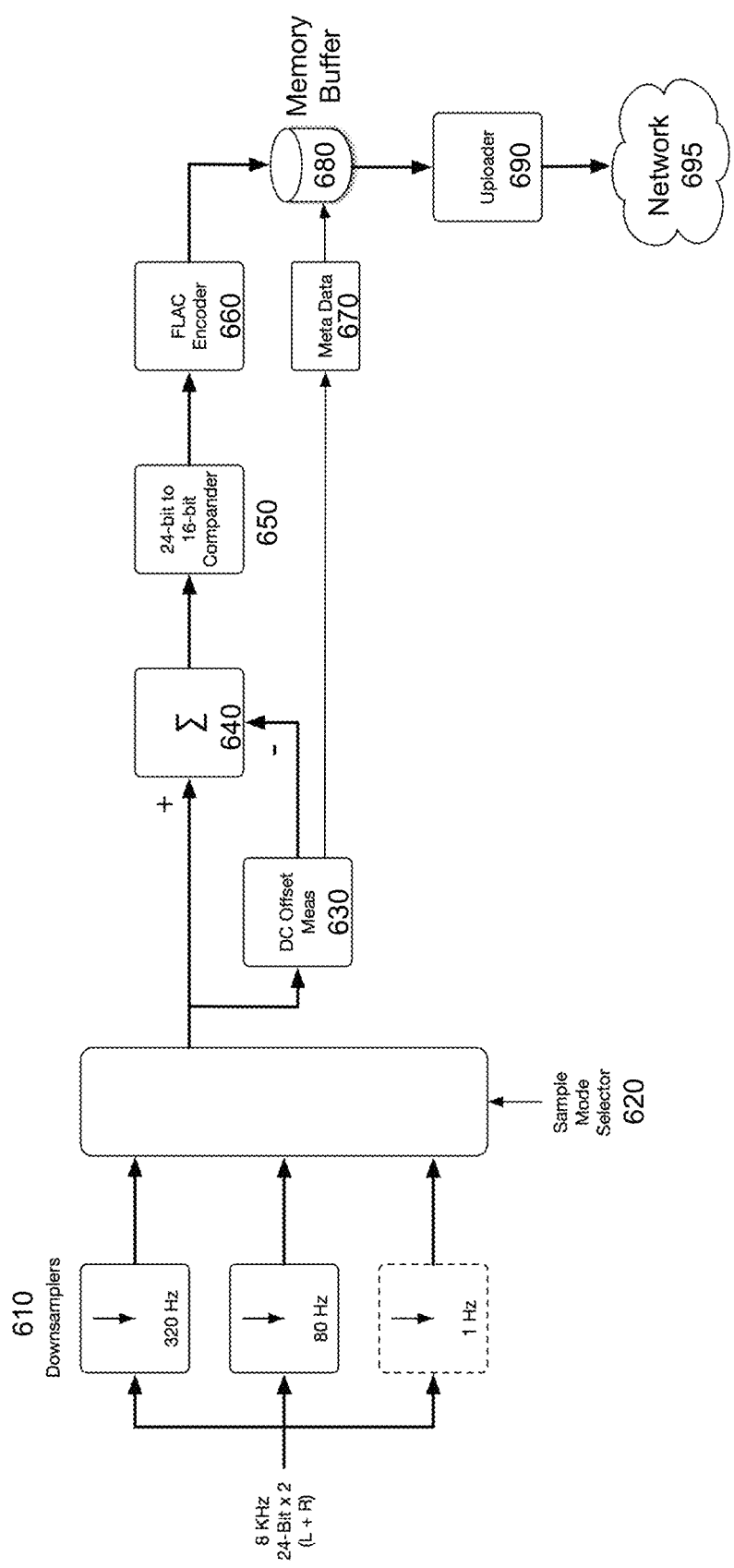
FIG. 6 is a block diagram of one embodiment of the digital portion of the receiver.

FIG. 6 is a block diagram of one embodiment of the digital portion of the receiver. The data from the A-to-D converter in one embodiment is 24-bit two channel data.

This is input into a downsampler 610, in one embodiment. In one embodiment, the receiver selects which downsampler to utilize. In one embodiment, the server controls the receiver's selection. In one embodiment, the selection is based on the data received and analyzed by the server.

The reason for sample rate selection is to optimize the upload based on a current state of the sleep monitor. In one embodiment, the sleep monitor states may include: not in use (no one on bed), in use for limited analysis, and in full use. For example, in one embodiment, if no one is on the bed, the rate can be downsampled to a lowest sample rate, for example between 0.5 and 5 Hz. In one embodiment, the lowest sample rate is 1-Hz. If only sleep-states and HR/BR measurements are being utilized, the sample rate can be reduced to a mid-range frequency, for example 30 to 100 Hz. In one embodiment, the midrange frequency is 80Hz. 80-Hz. Whereas, if sleep states, HR/BR, snore detection, respiratory events, HRV, etc., are being measured, a higher rate, for example 100 Hz to 500 Hz may be used. In one embodiment, the higher rate is a 320-Hz rate. In one embodiment, the sample mode selector 620 determines the sampling rate. In one embodiment, software services running on the cloud determine and remotely set the sample rate selection 620.

In one embodiment, a DC offset measurement 630 allows DC offset removal 640 (shown as an element labeled with a Greek letter sigma). The DC offset removal 640 is to allow the compander 650 to be as efficient as possible. In one embodiment, the DC offset is recorded with the FLAC data, as meta data 670, so that the server can re-add the DC offset after expanding (un-companding) the data.

The compander 650 is used to reduce the uploaded data size, removing non-essential values from the data stream.

The compressed data is then encoded, in one embodiment. In one embodiment, free lossless audio codec (FLAC) encoder 660 is used to encode the data. In another embodiment, another lossless compression algorithm may be used, such as MPEG-4 ALS. In other embodiments, alternative encoding may be used. In one embodiment a lossy compression, such as a variant of MP3 may be used. In such an embodiment, the compression may be tuned for the data content so that the loss is minimal.

The FLAC data is stored in a memory 680 and then uploaded by uploader 690, to server via a network 695. In one embodiment, the uploader 690 uploads bursts of data. In one embodiment, the upload interval is specified by the cloud servers. In another embodiment, the uploader 690 uploads data when a certain amount of data is accumulated. This may result in slower uploads for data with a lower sample rate.

In one embodiment, the digital portion of the system runs in firmware on a processor.

Figure 7:
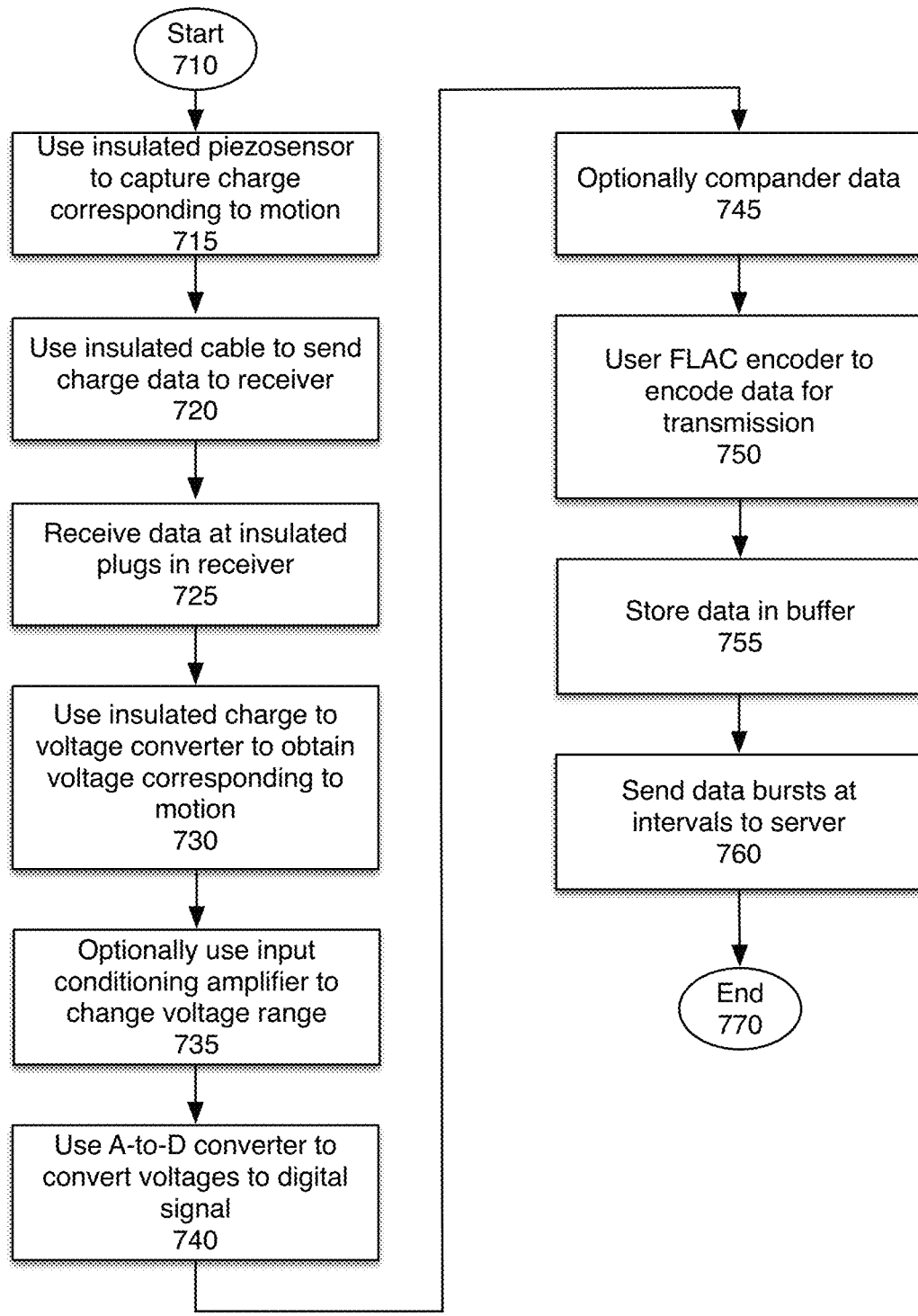
FIG. 7 is a flowchart of one embodiment of data collection through upload to the server.

FIG. 7 is a flowchart of one embodiment of data collection through upload to the server. The process starts at block 710. At block 715, insulated piezoelectric sensors are used to capture charge corresponding to motion. This data recording is sufficiently sensitive so that the data reflects not only body movements, but also the movement of the chest in breathing, as well as the movement of the rib cage in heart beats. The sensor is sensitive enough that it can record, and the AI-enabled system can identify, snoring based on the vibration of the user's throat, which is detected by the sensor.

The system, at block 720, uses an insulated cable to send the charge data to the receiver, in one embodiment. Because the data is very precise even a small amount of noise can reduce the precision sufficiently to create an issue. Therefore, the data from the time the sensor detects it, until it is converted to a voltage, is run through an insulated system.

The insulated cable connects the data to insulated plugs, where the data is received at block 725, in one embodiment. A charge-to-voltage converter is used to obtain a voltage corresponding to the charge data, reflecting the motion sensed by the sensors, at block 730. Optionally, at block 735, a conditioning amplifier may be used to adjust the voltage range for the A-to-D converter.

At block 740, the A-to-D converter converts the voltages to a digital signal. In one embodiment, the insulation may extend to the A-to-D converter. In another embodiment, once the signal is converted to a voltage, the signal is more robust, and the path need no longer be fully insulated.

At block 745, the data is compandered, in one embodiment.

At block 750, the data is encoded for transmission. In one embodiment, the encoding uses a lossless encoding algorithm. In one embodiment, a FLAC encoding is used. In one embodiment, this allows the use of an audio CODEC for the encoding.

At block 755, in one embodiment the data is stored in buffer. In one embodiment, at block 760 the data is sent in bursts to the server. In another embodiment, the data may be sent continuously. In another embodiment, the data may be sent periodically. The process then ends at block 770.

Of course, though this is shown as a flowchart, in one embodiment it is implemented as an interrupt-driven system, such that the device state is changed when a state detection system identifies a change of the state. Additionally, the ordering of state checking is arbitrary.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A hardware sleep sensor system comprising:
    a piezo sensor outputting charge data corresponding to a motion;
    an insulated cable from the piezo sensor to a receiver, to transmit the charge data;
    a charge to voltage converter on the receiver, the charge to voltage converter for converting the charge data to voltage data;
    an analog-to-digital converter to convert the voltage data to digital data;
    an uploader to upload the digital data to a server for processing, the server to determine a level of use of the sleep sensor system; and
    a downsampler configured to receive a down-sampling rate calculated based on the level of use of the sleep sensor system, wherein the level of use is one of: not in use, limited analysis use, and full use;
    the downsampler further configured to down-sample the output of the analog-to-digital converter using the down-sampling rate, and provide the down-sampled data to the uploader.

2. The system of claim 1, further comprising:
    an insulated plug in the receiver to connect the insulated cable to the receiver.

3. The system of claim 1, wherein the charge to voltage converter is insulated.

4. The system of claim 1, wherein the piezo sensor, a plug in the receiver connected to the insulated cable, and the charge to voltage converter are on an insulated portion of the receiver.

5. The system of claim 4, wherein the insulated portion of the receiver is insulated with a metal enclosure.

6. The system of claim 1, further comprising:
an electrostatic discharge protector coupled to the insulated cable.

7. The system of claim 1, wherein the analog-to-digital converter converts analog voltage data to digital voltage data and outputs the digital voltage data to a lossless algorithm to convert the digital voltage data to compressed data.

8. The system of claim 7, wherein the lossless algorithm is FLAC (Free Lossless Audio Codec), and the analog-to-digital converter is an audio codec.

9. The system of claim 1, wherein the piezo sensor comprises two piezo sensors outputting charge data; and
wherein the analog-to-digital converter is a two-channel converter to provide concurrent sampling of the charge data from the two piezo sensors.

10. The system of claim 1, wherein the down-sampling rate is one of a plurality of selectable down-sampling rates and wherein:
the not in use level is defined as no user data being measured;
the limited analysis use level is defined as measuring: sleep state, heart rate and breathing rate; and
the full use level is defined as measuring the sleep state, the heart rate, and the breathing rate, and further measuring one or more of: snore detection, respiratory events, and heart rate variability.

11. The system of claim 10, wherein: the down-sampling rate is 0.5 Hz to 5 Hz for the not in use level; is 30 Hz to 100 Hz for the limited analysis use level; and is 100 Hz to 500 Hz for the full use level.

12. A hardware sleep sensor system comprising a receiver to upload data to a server for analysis, the receiver comprising:
an insulated plug to receive an insulated cable, the insulated cable carrying charge data from a piezo sensor;
a charge to voltage converter for converting the charge data to voltage data;
an analog-to-digital converter to convert the voltage data to digital data;
a down-sampler configured to receive a down-sampling rate, the down-sampling rate calculated based on a current level of use of the sleep sensor system, the current level of use being one of: not in use level, limited analysis use level, and full use level, the down-sampler further configured to down-sample the digital data using the down-sampling rate; and
an uploader to upload the down-sampled digital data to a server for processing, the server to determine the current level of use of the sleep sensor system, based on the down-sampled digital data.

13. The system of claim 12, further comprising:
an electrostatic discharge protector coupled to the insulated cable.

14. The system of claim 12, wherein the analog-to-digital converter comprises a FLAC audio codec that implements lossless compression of the voltage data to digital data.

15. The system of claim 12, wherein the piezo sensor comprises:
two piezo sensors outputting charge data; and
wherein the analog-to-digital converter is a two-channel converter to provide concurrent sampling of the charge data from the two piezo sensors.

16. The system of claim 15, wherein:
the not in use level is defined as no user data being measured;
the limited analysis use level is defined as measuring one or more of: sleep state, heart rate, and breathing rate; and
the full use level is defined as measuring the sleep state, the heart rate, and the breathing rate, and further measuring one or more of: snore detection, respiratory events, and heart rate variability.

17. A hardware sleep sensor system comprising:
a piezo sensor outputting charge data corresponding to a motion;
an insulated cable from the piezo sensor to a receiver, to transmit the charge data;
the receiver comprising:
a charge to voltage converter on the receiver, the charge to voltage converter for converting the charge data to voltage data;
an analog-to-digital converter to convert the voltage data to digital data;
an uploader to upload the digital data to a server for processing;
a server to analyze the digital data to determine a user's sleep status, and to send control signals to the receiver; and
a downsampler, to down-sample the output of the analog-to-digital converter and provide the down-sampled data to the server, wherein the down-sampler is configured to receive a down-sampling rate selected from a plurality of selectable down-sampling rates, the received down-sampling rate selected based on a current level of use of the sleep sensor system as determined by the server, the current level of use being one of: not in use level, limited analysis use level, and full use level.

18. The hardware sleep sensor system of claim 1, wherein the uploader uploads the digital data to the server at an upload time interval specified by the server.

19. The hardware sleep sensor system of claim 1, wherein the uploader uploads the digital data to the server when a predetermined amount of digital data is accumulated by the uploader.

20. The system of claim 1, wherein the uploader receives data from the server indicating a current state of the hardware sleep sensor system and the uploader is configured to determine the down-sampling rate in accordance with the current level of use of the hardware sleep sensor system, wherein:
the not in use level is defined as no user data being measured;
the limited analysis use level is defined as measuring: sleep state, heart rate and breathing rate; and
the full use level is defined as measuring the sleep state, the heart rate, and the breathing rate, and further measuring one or more of: snore detection, respiratory events, and heart rate variability.

* * * * *